United States Patent [19]
Kaiser

[11] Patent Number: 5,968,807
[45] Date of Patent: Oct. 19, 1999

[54] CULTURE MEDIA CONTAINING GLYCEROL THAT ARE PH AND COLOR STABLE WHEN HEAT STERILIZED

[75] Inventor: James Jay Kaiser, Rochester, N.Y.

[73] Assignee: Getinge/Castle, Inc., Rochester, N.Y.

[21] Appl. No.: 07/837,666

[22] Filed: Feb. 14, 1992

Related U.S. Application Data

[63] Continuation of application No. 07/067,001, Jun. 29, 1987, abandoned.

[51] Int. Cl.$^6$ ............... C12N 1/20; C12Q 1/22; C12M 1/34
[52] U.S. Cl. ............ 435/253.6; 435/31; 435/243; 435/289.1; 435/297.1; 435/304.1
[58] Field of Search ............... 435/29, 31, 34, 435/253.6, 243, 289.1, 297.1, 304.1

[56] References Cited

U.S. PATENT DOCUMENTS

| | | | |
|---|---|---|---|
| 2,950,202 | 8/1960 | Brockmann | 99/192 |
| 4,291,122 | 9/1981 | Orelski | 435/31 |

OTHER PUBLICATIONS

Atkinson, et al., J. Applied Bacteriology, vol. 38, No. 3 1975, pp. 301–304.
Jenness, et al., Principles of Dairy Chemistry, John Wiley & Sons, N.Y., 1959, pp. 346–349.

*Primary Examiner*—David M. Naff
*Attorney, Agent, or Firm*—Phillips, Lytle, Hitchcock, Blaine & Huber, LLP

[57] ABSTRACT

A heat stable culture medium is prepared by substituting glycerol for carbohydrate components such as dextrose that are prone to Maillard reactions. A preferred medium contains pancreatic digest of casein, soytone, soluble starch, a phosphate buffer system, a salt, a pH indicator, and glycerol as a primary carbon source. The culture medium is pH and color stable when exposed to steam sterilization, including post-manufacture steam sterilization when used as the medium of a self-contained biological indicator. A self-contained sterility indicator device contains a flexible cylindrical tube having an opening at one end. The tube contains a submicron screen as a gas transmissive, bacteria impermeable window, an adsorbent wick bearing at one end viable microorganisms, and a frangible glass ampule containing the culture medium. The end of the wick containing microorganisms is located away from the ampule and adjacent the screen. A cap that seals the tube opening has an open position, and a closed position that seals the window and prevents media evaporation. During sterilization, the microorganisms adjacent the screen are exposed directly to sterilant. After sterilization, the cap is moved to the closed position, and the ampule is broken by applying pressure to sides of the flexible tube to release the culture medium. The medium is adsorbed by the wick and transported to the end containing microorganisms. After incubation, the device is examined to determine from the color of the indicator whether or not microorganism growth has occurred.

12 Claims, 1 Drawing Sheet

CULTURE MEDIA CONTAINING GLYCEROL THAT ARE PH AND COLOR STABLE WHEN HEAT STERILIZED

RELATED APPLICATIONS

This application is a continuation of application Ser. No. 07/067,001, filed Jun. 29, 1987, now abandoned.

BACKGROUND OF THE INVENTION

Microbial growth media provide a nutrient chemical environment for the growth of microorganisms. Microbial growth media are typically composed of water, protein digests and/or extracts, carbohydrates, minerals, a buffer system, and a pH indicator in certain applications. Additional metabolites may be included to influence metabolic pathways. Microbial growth media are made from non-sterile components and are sterilized in the last stages of their fabrication. This is commonly done by heat or filtration.

When the means of sterilization is heat, carbohydrate growth media components are prone to change. It is well known that heating microbial growth media causes carbohydrate degradation and subsequent acidification of growth media. The degree of degradation is a function of the heat applied, the carbohydrate concentration, the starting pH, and the type of carbohydrate present. Carbohydrates can react with amino acids, peptides, and proteins to form brown melanoidins. These are termed Maillard reactions and can result in the destruction of essential nutrients in growth media and color darkening. One class of carbohydrates commonly employed with microbiological growth media is monosaccharides. Monosaccharides, such as the six carbon dextrose, are particularly prone to heat induced Maillard reactions.

U.S. Pat. No. 4,291,122 to Orelski, which is incorporated herein by reference, describes features of microbial growth media as applied to unitary or self-contained biological indicators. Media used in these indicators must support the growth of either *Bacillus stearothermophilus* in monitoring steam sterilization processes, or *Bacillus subtilis* in monitoring ethylene oxide sterilization processes. Self-contained biological indicators employ a visual pH indicator that is dissolved in a medium. As the pH of the medium shifts (due to presumed bacterial growth), the color of the media will change, thus simplifying the visual reading of this device.

Growth of *Bacillus stearothermophilus* causes growth media to become acidic. *Bacillus subtilis* growth causes growth media to acidify only in the presence of sufficient carbohydrates. Once carbohydrates are consumed, protein components are catabolized. The catabolism of proteins causes growth media to become basic, thus causing the pH indicator that had initially changed color to signify growth, to return to its original color. This process of depleting carbohydrates and consuming excessive protein and causing the pH indicator to return to a false non-growth color is called reversion. One must provide sufficient carbohydrate in media to avoid reversion and at the same time avoid the media degrading Maillard reactions. If a self-contained biological indicator is used to monitor a steam sterilization process, the indicator medium would thus be heated a second time during its actual use in addition to its original sterilization in manufacture. Orelski taught that partitioning carbohydrates from the rest of the liquid medium components avoids the damaging Maillard reactions. In the Orelski teaching, carbohydrates are mixed with the rest of the medium only when the self-contained biological indicator is activated. There is other evidence in the prior art for separate sterilization of carbohydrate components of microbial growth media, but not for this specific application.

SUMMARY OF THE INVENTION

The present invention is directed to microbial culture media being pH and color stable in steam sterilization. More specifically, the invention is directed to the discovery that the use of glycerol in place of carbohydrates such as the monosaccharide-dextrose in microbial culture media results in media that are pH and color stable when repeatedly steam sterilized. Although not defined as a carbohydrate, glycerol is metabolized through similar metabolic pathways. As described above, U.S. Pat. No. 4,291,122 describes microbial culture media with carbohydrate components that are physically isolated from the remaining portion of the culture media in order to prevent the unwanted acidic products from Maillard reactions. The acidic products cause an undesired color change in the pH indicator, thus resulting in an ambiguous reading in the absence of microbial growth for self-contained biological indicators.

The invention broadly includes a heat stable culture medium formulation which substitutes glycerol for carbohydrate components prone to Maillard reactions. This culture medium formulation typically contains protein digests, minerals, a pH indicator, and glycerol. Such culture medium is pH and color stable when compared before and after exposure to steam sterilization processes.

One culture medium formulation of the present invention includes pancreatic digest of Casein, soytone, soluble starch, a phosphate buffer system, a salt, a pH indicator, and glycerol in a concentration to act as the primary carbon source to support microbial growth. The culture medium is pH and color stable when compared before and after exposure to steam sterilization processes. This formulation will typically contain glycerol in a concentration of about 1 to 20 grams per liter of water.

The present invention makes unnecessary the separation of components and provides for media that do not exhibit the acidic breakdown associated with Maillard reactions. This allows for a significant improvement in ease of maintenance, as well as avoiding problems related to incomplete mixing of the separate media components.

Other features and advantages of the present invention will become apparent from the following description taken in conjunction with the accompanying drawings.

DETAILED DESCRIPTION OF THE INVENTION

Figure 1:
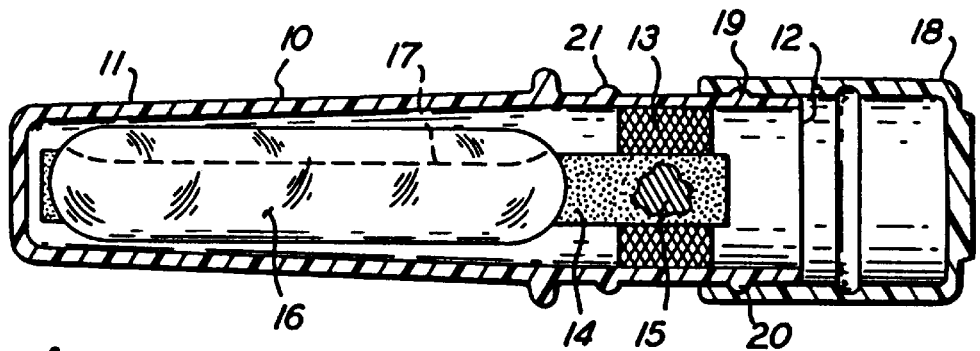
FIG. 1 is a longitudinal sectional view of one embodiment of a device which may be used with the present invention.

The present invention is directed to a microbial culture formula or medium which exhibits pH and color stability as compared before and after exposure to a steam sterilization process. The preferred application of the present invention is in conjunction with pH indicators and media formulations. pH indicators are commonly used for growth detection of microflora in biological indicators. Avoidance of Maillard reactions during a steam sterilization process results in color and pH stable media. Broadly, the present invention comprises culture media formulations which contain protein digests, minerals, a pH indicator, and glycerol, with said media being pH and color stable when compared before and after exposure to a steam sterilization process.

Three examples of specific growth media are illustrated as follows: Medium I is a typical prior art formulation which uses the monosaccharide carbohydrate-dextrose, while Media formulations II and III represent media of the present invention. The constituents are quantified in grams per liter of water.

TABLE

| Constituent | I. Prior Art Media | II. Present Invention | III. Present Invention |
|---|---|---|---|
| Pancreatic digest of Casein | 5.7 | 5.0 | 5.8 |
| Soytone | 1.0 | 1.0 | 1.0 |
| Dextrose | 3.8 | none | 0.1 |
| Soluble Starch | 1.0 | 1.0 | 1.0 |
| Glycerol | none | 12.5 | 7.6 |
| $K_2HPO_4$ | 1.5 | 1.5 | 1.5 |
| NaCl | 4.0 | 4.0 | 5.0 |
| Phenol Red | 0.010 | 0.018 | 0.010 |
| L-Valine | none | 0.5 | none |
| DL-Isoleucine | none | 0.5 | none |

The various functions of the constituents of the above media are as follows:

Pancreatic digest of Casein is a milk derived protein digest. Soytone is a soya bean digest. Other digests or extracts may be used. In general they provide a) carbohydrates, b) inorganic ions, c) purines and pyrimidines (nucleic acid components to facilitate population growth), d) essential vitamins, and e) amino acids and peptides (nitrogen nutritional source). The carbohydrates found in common extracts are at trace levels and are supplemented by additional carbon sources to improve growth characteristics of media. The monosaccharide-dextrose and the non-carbohydrate glycerol are examples of simple carbon sources that are easily metabolized. Without a readily available source of simple carbon sources to be oxidized and provide energy, microorganisms would have to spend energy and time to break down more complex carbon sources. $K_2HPO_4$ (dibasic potassium phosphate) serves two purposes. It provides buffering capacity to media, and provides phosphates for metabolic processes. Buffers are chemicals added to solutions that help stabilize the pH. The buffering capacity of $K_2HPO_4$ and other components found in the three media is insufficient to modulate the effects of Maillard reactions. Sodium chloride (NaCl) is an inorganic salt-mineral supplement that also is added to modulate the osmotic strength of media. Phenol Red (phenolsulfonphthalein) is one example of an acid-base indicator that provides a visual response to changes in pH and therefore presumed microorganism growth. Other suitable indicators include bromocresol purple and bromothymol blue. L-Valine and DL-isoleucine are amino acids included to improve *Bacillus subtilis* germination and inhibit reversion. Soluble starch is added because it has been claimed to absorb various inhibitory growth factors that may be in media. It is a commonly recognized practice to adjust the pH of media by adding trace quantities of HCl or NaOH solutions in the formulation stage.

It has been demonstrated that a heat-sterilization-induced pH shift is common to microbial growth media that employ monosaccharide carbohydrates as the primary carbon source. If one exposes Medium I of the above Table to the steam sterilization equivalent to 14 minutes at 250° F., the pH of the medium will drop from 8.3 to 7.2. Additional heating causes further pH lowering. The Medium III changes approximately 0.2 pH units from 7.6 to 7.4 following exposure to the steam sterilization equivalent to 14 minutes at 250° F., while Medium II, which has an initial pH of 7.6, changed less than 0.1 pH units when exposed to identical conditions.

In some applications, a limited pH shift due to trace monosaccharide carbohydrate presence can be tolerated. In these instances, substitution with glycerol may be done as exemplified by Medium III which contains 0.1 grams per liter of dextrose.

The incorporation of glycerol and reduction of monosaccharides minimizes the media degrading Maillard reactions and promotes the stability of the pH color indicator by maintaining a stable pH. Having a material which is less sensitive to processing heat conditions is a tangible improvement in the state of the art. This advantage is more important when applied to self-contained biological indicators. Since self-contained biological indicators are intended to be exposed to post-manufacture steam sterilization, replacing monosaccharides such as dextrose with glycerol is a significant benefit, and is a major improvement of the existing art.

Another example of the pH and color stability in steam sterilization of glycerol based media of the present invention is exhibited by the following formulation:

| Constituent | Grams/Liter |
|---|---|
| Glycerol | 7.5 |
| Pancreatic digest of Casein | 5 |
| Soytone | 1 |
| Soluble Starch | 1 |
| Dibasic Potassium Phosphate | 1.5 |
| Sodium Chloride | 4 |
| DL-Isoleucine | 0.5 |
| L-Valine | 0.5 |
| Phenol Red | 0.018 |

The pH of the above solution was 7.40 after formulation. After a 250° F. 20 minute steam sterilization, the pH remained stable at 7.43. After an additional 60 minutes of 250° F. steam exposure, the pH became 7.40. Throughout this experiment, the color of the sterilized medium was compared to unsterilized samples. There was no significant color change detected from the original color of the medium, even after the 80 minutes of steam exposure. By comparison, a 30 minute 250° F. steam exposure caused the dextrose-based Medium I to turn orange due to acidic products generated from Maillard reactions.

In applications of the present invention, glycerol should be present in a concentration sufficient to provide an adequate simple carbon source to support microbial growth. A concentration up to about 20 grams per liter has proved to be satisfactory. A suitable concentration range is from about 1 to 20 grams per liter, and in some situations, concentrations outside this range can also be used.

Broadly, typical culture media of the present invention may comprise the following formulation in concentrations of grams per liter of water.

| Constituent | Grams/Liter |
| --- | --- |
| Protein Digests | 5.0–7.0 |
| Glycerol | 1.0–20.0 |
| Buffering Agent | 0.5–2.0 |
| pH Indicator | 0.0–0.018 |
| Inorganic Salts | 3.0–6.0 |
| Amino Acids | 0.0–1.5 |

A specific typical culture medium of the present invention with suitable ranges is listed below in concentrations of grams per liter of water:

| Constituent | Grams/Liter |
| --- | --- |
| Pancreatic digest of Casein | 5.0–7.0 |
| Soytone | 0.5–1.5 |
| Glycerol | 1.0–20.0 |
| Dipotassium Phosphate | 0.5–2.0 |
| Phenol Red (phenol sulfonphthalein) | 0.008–0.018 |
| Sodium Chloride | 3.0–6.0 |
| Amino Acids as exemplified by L-Valine and DL-isoleucini | 0.0–1.5 |

Other examples of the culture medium include:

A. A culture medium which comprises in grams per liter of water:

| Constituent | Concentration |
| --- | --- |
| Pancreatic digest of Casein | 5.0 |
| Soytone | 1.0 |
| Soluble starch | 1.0 |
| Glycerol | 12.5 |
| $K_2HPO_4$ | 1.5 |
| NaCl | 4.0 |
| Phenol Red | 0.018 |
| L-Valine | 0.5 |
| DL-Isoleucine | 0.5 |

B. A culture medium which comprises in grams per liter of water:

| Constituent | Concentration |
| --- | --- |
| Pancreatic digest of Casein | 5.8 |
| Soytone | 1.0 |
| Dextrose | 0.1 |
| Soluble starch | 1.0 |
| Glycerol | 7.6 |
| $K_2HPO_4$ | 1.5 |
| NaCl | 5.0 |
| Phenol Red | 0.010 |

Typical culture media will include in grams per liter of water:

| Constituent | Concentration |
| --- | --- |
| Protein digests | 5.0–7.0 |
| Glycerol | 1.0–20.0 |
| Buffering agent | 0.5–2.0 |
| pH indicator | 0.000–0.018 |
| Inorganic salts | 3.0–6.0 |
| Amino acids | 0.0–1.5 |

Figure 2:
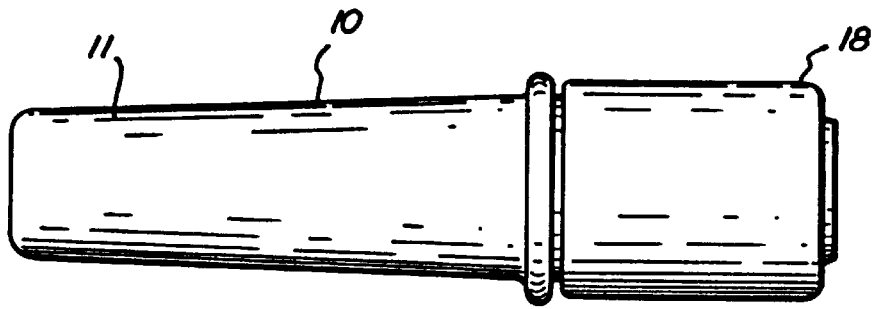
FIG. 2 is a side elevation view of the device of FIG. 1 with the closure member in the closed position.
Figure 3:
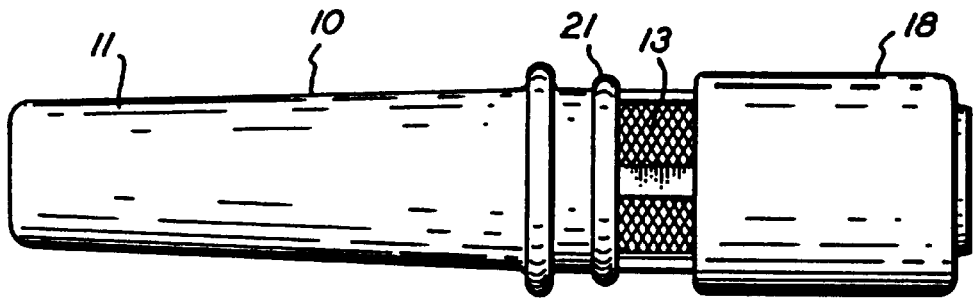
FIG. 3 is a side elevation view of the device of FIG. 1 with the closure member in the open position.

Media of the present invention have a preferred application in a unitary or self-contained sterility indicator device such as that illustrated on FIG. 1 of the drawings. The device has an outer compartment comprising a flexible transparent or translucent, cylindrical tube 10, having substantially non-gas absorptive and liquid-impermeable walls 11 and an open end 12. Compartment 10 further contains a gas transmissive, bacteria impermeable window in the form of a submicron screen or other suitable material 13 at one end thereof. Compartment 10 further contains a suitable carrier such as absorbent wick 14 bearing a predetermined number of viable microorganisms, or bacterial spores. The microorganisms, illustrated by shaded area 15, are in one embodiment confined to one end of wick 14. Compartment 10 also contains, in coacting relationship therewith, a normally sealed, pressure-openable inner compartment 16, such as a frangible glass ampule, containing an aqueous culture medium of the present invention illustrated by dotted line 17 which is capable, with incubation, of promoting growth of the microorganism when contacted therewith. The end of the wick containing the microorganisms is located away from the medium containing ampule and adjacent to screen 13. A substantially non-gas absorptive and liquid-impermeable closure member or cap 18 is provided to seal the open end 12 of compartment 10. In FIGS. 1 and 3, the cap is shown in the open position and is engaged to be moved to a second or closed position illustrated in FIG. 2. In the closed position the permeable window is sealed, thus preventing the evaporation of media. As shown, the cap 18 is engaged in a pressure snap fit relationship with compartment 10 by recess 19 engaging ridge 20. To close the cap, longitudinal pressure forces the flexible sidewalls of the cap to expand or deflect slightly and allow the cap to move to a second or closed position in which recess 19 now engages ridge 21.

The medium 17 also contains a pH indicator material (not shown) which undergoes a visible color change in response to growth of the microorganisms. During sterilization the microorganisms located in a position opposite the screen are exposed to direct impingement of the sterilant. Upon completion of the sterilization process, the device is removed, the cap is moved to the closed position and the medium-containing ampule is broken by applying pressure through the flexible side of the device releasing the culture medium into the compartment. The culture medium is absorbed by the carrier material and transported to the end of the carrier containing the microorganisms.

The device is then placed into an incubator or other constant temperature environment to permit the growth of any surviving microorganisms. After a suitable growth period, the device is examined to determine from the color of the indicator whether or not growth had taken place.

Microorganisms not killed during the sterilization process will begin to germinate and grow during incubation. Due to metabolism of selected media components, this growth causes a shift in pH, and the pH indicator material to change color. This color change is observed through the transparent/translucent walls of compartment 10, and indicates to an observer that the sterilization cycle had not killed all of the microorganisms on the wick and hence was insufficient to assure sterilization of the other items in the sterilizer. An absence of a color change indicates that the sterilization cycle had killed all of the microorganisms on the wick and was sufficient to assure sterilization of the items introduced to the sterilizer.

The media of the present invention should not be limited to use with self-contained biological indicator applications. The glycerol-based system can also be applied to a culture medium containing a pH indicator that is sold in individual tubes for the recovery of aseptically transferred biological indicators. The Castle Company TEC-TEST® Biological Indicator Culturing Set exemplifies such an application. A further application would be the use of this invention with an ampule-based self-contained biological indicator. A device of this type called Chemspore, sold by the American Sterilizer Company is an example of an ampule-based self-contained biological indicator which may be exposed to multiple sterilizations. In general, by eliminating the Maillard reactions, heat exposure in steam sterilizing microbial growth media in manufacturing or subsequent use becomes less critical. Because a glycerol-based system is more heat stable, it is also less sensitive to storage and shipping conditions which may create problems for various media that will not be multiply sterilized.

As stated earlier, the preferred application of this invention is in conjunction with pH indicators to provide a visible sign of microorganism growth. The color change, rendered to media by pH indicators in response to pH shifts caused by growth, simplifies detection of that growth. Another means of detecting microorganism growth is through visual observation of media turbidity. Growth causes an increase in turbidity. Turbidimetric growth observations may be done on media which do not contain pH indicators. It is particularly important for media without pH indicators to be clear so as to avoid masking of growth induced turbidity. Maillard reaction products and subsequent media browning may hinder turbidimetric observations of media. This is especially true if an automated—optical means is employed to measure turbidity. It is recognized that the benefits of this invention, the avoidance of Maillard reactions through the substitution of glycerol for monosaccharides, may be applied to media that do not contain pH indicators as a mean of microorganism growth detection.

While the invention has been described in detail with respect to specific embodiments thereof, it will be understood by those skilled in the art that variations and modifications may be made without departing from the essential features thereof.

I claim:

1. A culture medium comprising a sterile admixture of water with protein digests, minerals, a pH indicator, and glycerol, said culture medium being pH and color stable after exposure to a subsequent heat sterilization process.

2. A culture medium which comprises a sterilized mixture of water, pancreatic digest of Casein, soytone, soluble starch, a phosphate buffer system, a salt, a pH indicator, and glycerol in a concentration sufficient to serve as the primary carbon source to support microbial growth, said culture medium being pH and color stable when exposed to a subsequent heat sterilization process.

3. The culture medium of claim 2 in which the glycerol is present in a concentration of about 1 to 20 grams per liter of culture medium.

4. A sterilized culture medium formulated to be pH and color stable after exposure to at least one subsequent heat sterilization, said sterilized culture medium comprising an admixture of water, protein digests, soluble starch, a pH buffering component, a salt, and glycerol in a concentration sufficient to support microbial growth.

5. The sterilized culture medium of claim 4, wherein said subsequent heat sterilization is a steam sterilization.

6. The sterilized culture medium of claim 4, further including a pH indicator.

7. The sterilized culture medium of claim 6, wherein said pH buffering component is a phosphate buffer.

8. A culture medium which has undergone first and second sterilizations, said second sterilization being a heat sterilization, and said culture medium comprising a mixture of water, protein digests, soluble starch, a pH buffer compatible with microbial growth, a salt, a pH indicator, and glycerol in an amount sufficient to support visually detectable microbial growth, said culture medium being pH and color stable during and after said heat sterilization.

9. A culture medium for use in a unitary sterilization monitoring device, comprising a sterile admixture of water, protein digests, soluble starch, a phosphate buffer, a salt, and glycerol in an amount sufficient to support visually detectable microbial growth, said culture medium being pH and color stable to repeated subsequent heat sterilizations.

10. A twice sterilized culture medium comprising an admixture of water with protein digests, minerals, a pH indicator, and glycerol, wherein said first sterilization is by heat or filtration and said second sterilization is by heat, said culture medium being pH and color stable following said first sterilization.

11. The culture medium of claim 10, wherein said protein digests comprise a pancreatic digest of casein, said minerals comprise a salt and a phosphate buffer system, said glycerol is present in a concentration sufficient to serve as the primary carbon source to support microbial growth, and further including soytone and soluble starch.

12. The culture medium of claim 11, wherein the glycerol is present in a concentration of between about 1 and about 20 grams per liter of water.

* * * * *